United States Patent
Ananth (10) Patent No.: US 9,463,328 B2
(45) Date of Patent: Oct. 11, 2016

(54) NANOPOWER VOLTAGE REFERENCE FOR AN IMPLANTABLE MEDICAL DEVICE

(71) Applicant: Cameron Health, Inc., San Clemente, CA (US)

(72) Inventor: Ravi S. Ananth, Laguna Niguel, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 588 days.

(21) Appl. No.: 13/914,885

(22) Filed: Jun. 11, 2013

(65) Prior Publication Data

US 2014/0361618 A1    Dec. 11, 2014

(51) Int. Cl.
| | |
|---|---|
| *H02M 3/06* | (2006.01) |
| *A61N 1/375* | (2006.01) |
| *A61N 1/378* | (2006.01) |
| *H02M 3/07* | (2006.01) |

(52) U.S. Cl.
CPC ............... *A61N 1/375* (2013.01); *A61N 1/378* (2013.01); *H02M 3/07* (2013.01); *Y10T 307/406* (2015.04)

(58) Field of Classification Search
CPC ....... A61N 1/375; A61N 1/378; H02M 3/07; Y10T 307/406
USPC .......................................................... 307/31
See application file for complete search history.

(56) References Cited

U.S. PATENT DOCUMENTS

| | | | | |
|---|---|---|---|---|
| 4,084,103 A * | 4/1978 | Burns, III | ............ | H02M 3/157 307/132 EA |
| 5,200,643 A * | 4/1993 | Brown | ................... | G05F 1/575 307/43 |
| 6,201,723 B1 * | 3/2001 | Farrington | .............. | H02J 1/102 363/147 |
| 6,215,288 B1 | 4/2001 | Ramsey et al. | | |
| 6,320,771 B1 * | 11/2001 | Hemena | .................. | H02J 1/102 323/272 |
| 6,647,292 B1 | 11/2003 | Bardy et al. | | |
| 7,414,453 B2 | 8/2008 | Tachibana et al. | | |
| 7,734,343 B2 | 6/2010 | Ransbury et al. | | |
| 7,782,039 B1 * | 8/2010 | He | ...................... | H02M 3/1588 323/224 |
| 8,330,536 B1 | 12/2012 | Quinn | | |
| 9,086,715 B2 * | 7/2015 | Riehl | ..................... | H02M 3/156 |
| 2002/0089313 A1 * | 7/2002 | Shashoua | ............... | H02M 3/07 323/209 |
| 2003/0066759 A1 * | 4/2003 | Hardee | ..................... | C25C 7/00 205/565 |
| 2005/0052154 A1 * | 3/2005 | Kavounas | .............. | H02J 7/345 320/116 |
| 2006/0097776 A1 * | 5/2006 | Wada | ...................... | H02M 3/07 327/544 |
| 2006/0273740 A1 * | 12/2006 | Saeueng | ................ | H02J 1/102 315/291 |
| 2007/0152737 A1 * | 7/2007 | Lin | ......................... | H02M 3/07 327/536 |
| 2008/0205093 A1 * | 8/2008 | Davies | .................. | H02J 3/1864 363/35 |
| 2008/0290666 A1 * | 11/2008 | Bourgeau | ............... | H02P 9/006 290/40 A |
| 2009/0323378 A1 * | 12/2009 | Melse | ..................... | H02M 3/07 363/60 |
| 2010/0013304 A1 * | 1/2010 | Heineman | ................ | G06F 1/26 307/31 |
| 2010/0013307 A1 * | 1/2010 | Heineman | ................ | G06F 1/26 307/33 |
| 2011/0068634 A1 * | 3/2011 | Kammeter | ............. | H02J 1/102 307/82 |
| 2011/0204961 A1 * | 8/2011 | Galal | ..................... | H02M 3/07 327/536 |
| 2012/0056479 A1 * | 3/2012 | Skinner | .................... | H02J 1/10 307/24 |
| 2012/0071043 A1 * | 3/2012 | Rembach | ............... | B63H 21/21 440/6 |
| 2014/0265885 A1 * | 9/2014 | Hu | ...................... | H05B 33/083 315/186 |

* cited by examiner

*Primary Examiner* — Jared Fureman
*Assistant Examiner* — Emmanuel R Dominique
(74) *Attorney, Agent, or Firm* — Seager, Tufte & Wickhem LLP (57) ABSTRACT

Capacitive charge re-distribution is used to create any desired number of secondary reference voltages from a primary reference voltage. The capacitive charge re-distribution allows reduced current consumption compared to conventional approaches to generating additional reference voltages. The secondary reference voltage or voltages may be greater than or less than the original reference voltage.

18 Claims, 7 Drawing Sheets

NANOPOWER VOLTAGE REFERENCE FOR AN IMPLANTABLE MEDICAL DEVICE

BACKGROUND

Active implantable medical devices use batteries to power their functionality. Batteries, however, have limited output capabilities, calling for reduced current consumption wherever possible. Such devices may include circuitry performing various different functions, including, for example, radio telemetry, therapeutic outputs, biological signal processing, alarm generation, memory storage, logic and other operations. This combination of several circuits can require provision of numerous reference voltages within a single device.

Independently creating such reference voltages can be highly power consumptive. For example, band-gap reference voltages may consume power on a constant basis. Zener diodes require a threshold level of current to operate in a stable zone. As a result, the number of independent references provided should be kept to a minimum to preserve power capacity.

A single voltage reference can be used to generate other references using multiplier or divider circuits. An example can be seen in U.S. Pat. No. 8,330,536, which shows a voltage divider providing several output voltage references in FIG. 2 of the patent.

Figure 1:
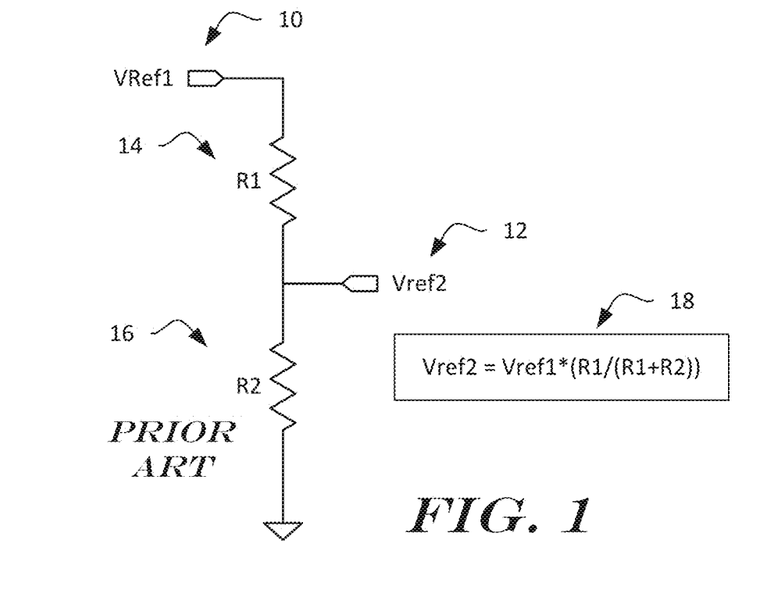
FIG. 1 illustrates a prior art voltage divider used to generate a second reference voltage from a first reference voltage.

For another example, FIG. 1 of the present disclosure illustrates the prior art use of a resistive divider circuit (first resistor R1 and second resistor R2) to generate a second reference voltage VRef2 from a first reference voltage VRef1. The problem is that this requires current flow through the resistors. Even with very large resistors, the current drawn will, over time, be a drain on the battery. Lower power alternatives are sought.

OVERVIEW

The inventor has recognized that improved and alternative circuits to provide one or more reference voltages off of a single reference are desired. In one illustrative embodiment, the present invention uses capacitive charge re-distribution to create any desired number of secondary reference voltages with from a primary reference voltage. The result is reduced current consumption. The reduction in current consumption can include reduced consumption relative to a voltage divider when the secondary reference is of a lower voltage than the primary. In addition, the use of switched capacitor circuitry allows the provision of secondary reference voltages that are higher than the primary reference voltage if needed, without requiring a voltage multiplier or other higher current consuming circuitry.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates a prior art voltage divider used to generate a second reference voltage from a first reference voltage. A first reference voltage 10 is able to provide a second reference voltage 12 by use of the resistive divider having resistors R1 14 and R2 16. The second reference voltage 12 is generated according to the formula shown at 18. In this example, however, current is always running through the resistors R1 14 and R2 16, costing power.

Figure 2:
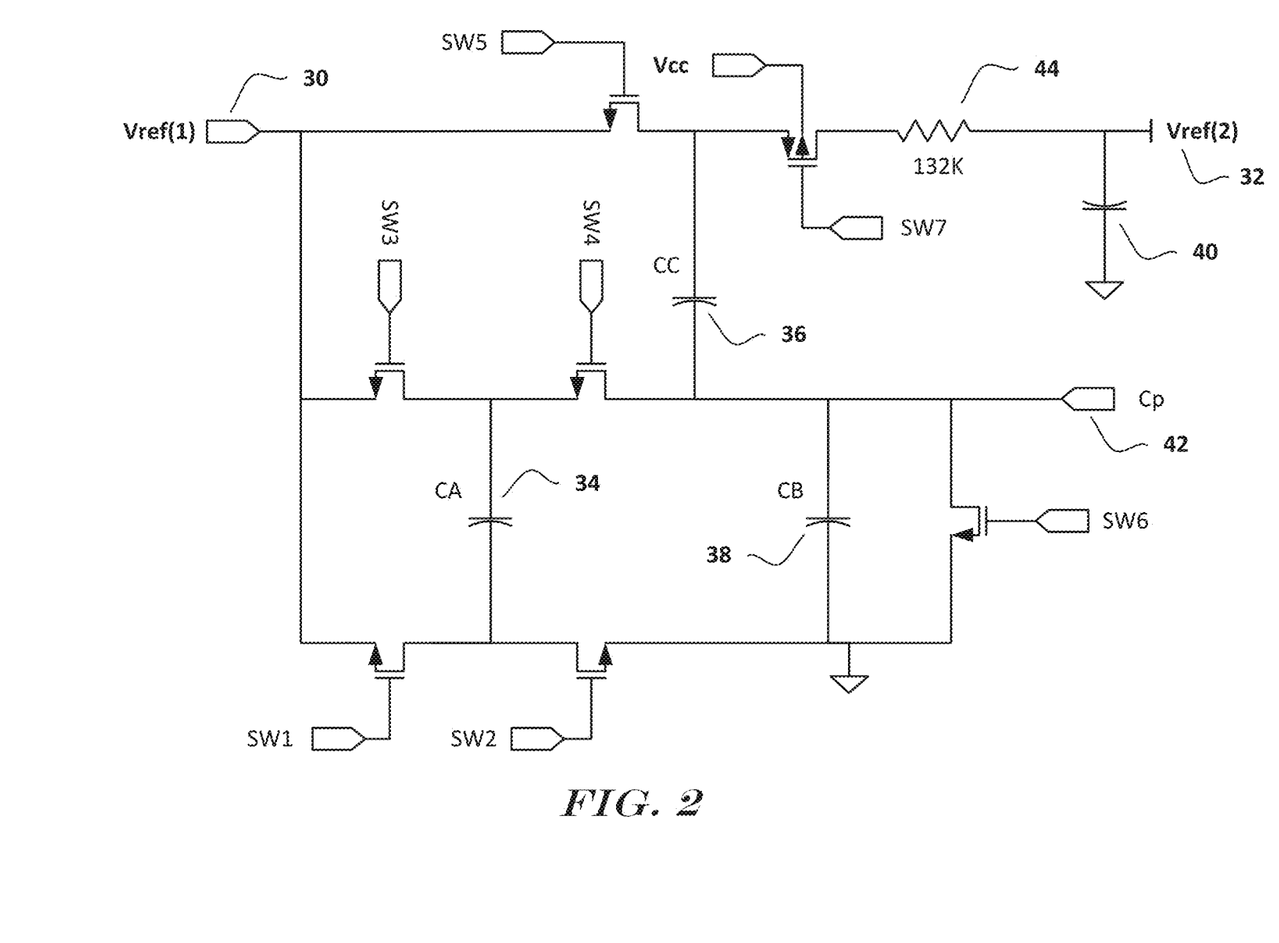
FIG. 2 shows an illustrative example of a circuit for providing a second reference voltage from a first using charge redistribution.

FIG. 2 shows an illustrative example of a circuit for providing a second reference voltage from a first using charge redistribution. In the example, the first reference 30 is used to provide a second reference voltage 32 on capacitor 40. This occurs with the use of three capacitors, CA 34, CB 38 and CC 36, and a switch network that includes switches SW1, SW2, SW3, SW4, SW5, SW6 and SW7. FIG. 2 reflects a working example for a low power system using small capacitors, and so the drawing accounts for parasitic capacitance at 42.

The relative sizing of the capacitors is as follows: CA is an 8X capacitor, CB 38 is a 4X capacitor, CC is a 16X capacitor, and CP is about 2X, where X is a general unit of capacitance. In the working example, X is about 590 femtofarads. Keeping the units of capacitance small will also reduce current consumption during operation of the circuit, but does increase the potential influence of parasitics. In the working example, the aim is to generate a second reference voltage 32 at 1.8 volts using an 850 mV first reference voltage 30. The manner of achieving this output is illustrated by FIGS. 3A-3C and summarized in Table 1:

TABLE 1

| Step | Closed | Open | Purpose |
| --- | --- | --- | --- |
| A | 2, 3, 5, 6 | 1, 4, 7 | Charge CA 34, CC 36; Zero CB 38; Isolate Cap 40 |
| B | 1, 4, | 2, 3, 5, 6, 7 | CA 34 reference to Vref(1) 30; Distribute charge from CA 34 to CB 38; Isolate Cap 40 |
| C | 1, 4, 7 | 2, 3, 5, 6 | After B, provide desired voltage to Cap 40 and Vref(2) 32 via 132K resistor 44 |

Figure 3A:
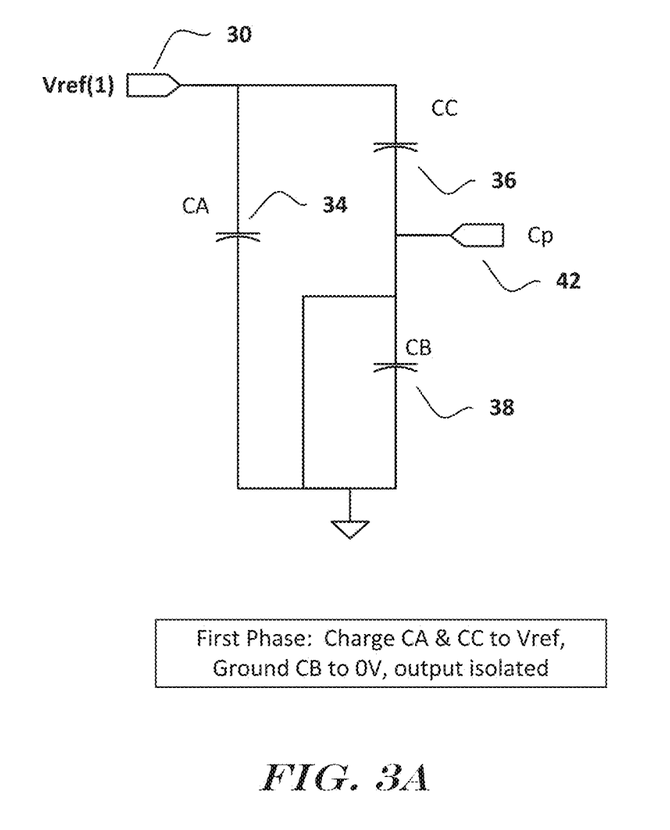
FIGS. 3A-3C are simplified depictions of the circuit of FIG. 2 in first, second and third states of operation.
Figure 3B:
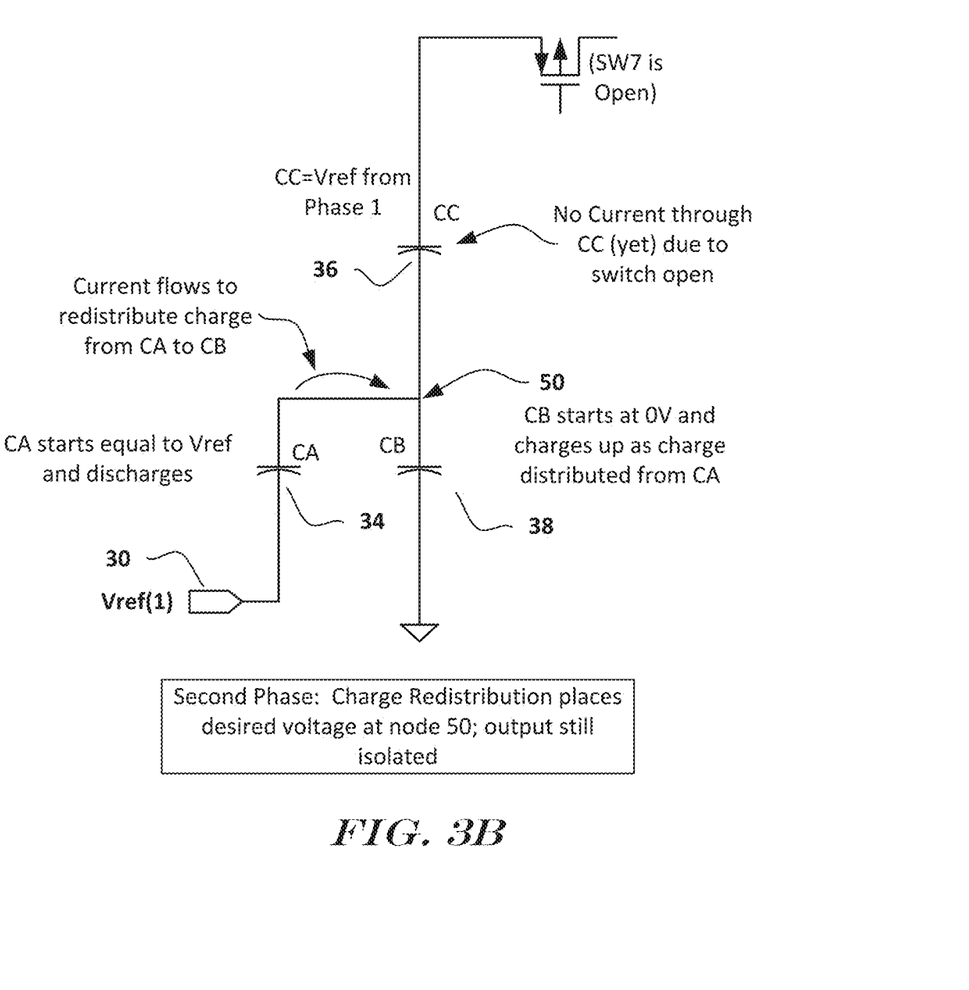
Figure 3C:
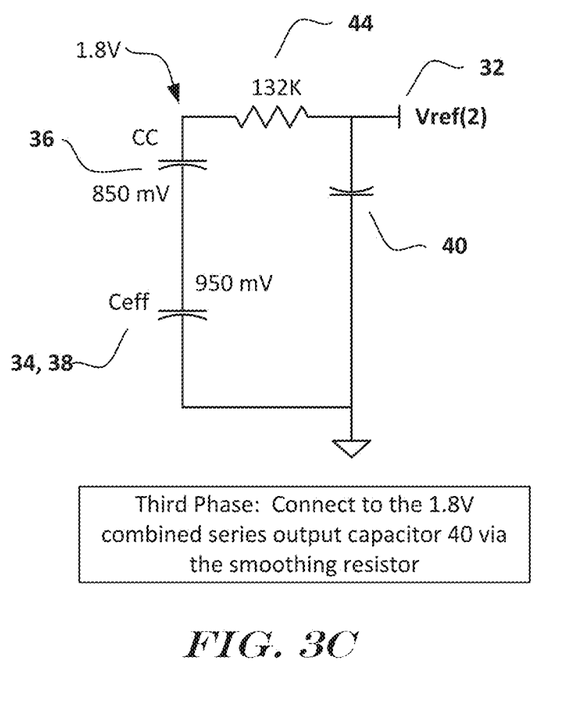

Turning to FIG. 3A, the Step A is shown in greatly simplified form. Vref(1) 30 is coupled to capacitors CA 34 and CC 36, which are each reference to ground. Capacitor CB 38 is zeroed by shorting both ends together to ground. The parasitic capacitance Cp 42 is illustrated as well and is provided, in this model, as if it attaches adjacent to capacitor CC 36. Those skilled in the art will understand the various ways that a parasitic capacitance can be modeled in view of a given circuit layout.

As noted Cp 42 is accounted for in the working example but may be omitted from the model if capacitors that are much larger than the parasitics are chosen. However, larger capacitors will use more current in some embodiments. Such considerations as manufacturability, reliability and the tolerance allowed can be assessed to determine the overall size to be used. In accomplishing the actual output voltage, however, ratios of capacitor sizes to one another (and parasitics, as the case may be) will determine the ratio of the first reference voltage to the output second reference.

The circuit remains in the first phase long enough to bring CA 34 and CC 36 to a level that approximates Vref(1) 30 in view of the non-ideal characteristics of the circuit (i.e. series resistance of traces and components). In the working example, a two phased, non-overlapping 1 kHz clock is used. Next, several switches are manipulated as noted above in Table 1, yielding the result shown by FIG. 3B.

In FIG. 3B, capacitor CA 34 is now referenced to Vref(1) 30. Capacitor CB 38, which was zeroed out previously, is now referenced to ground and connected to the high side of capacitor CA 34, causing current to flow and redistribute charge between the two capacitors CA 34 and CB 38.

If, for example, CA 34 is a larger capacitor than CB, the end result of the stage shown at FIG. 3B will be a voltage larger than Vref(1) 30 on CB 38, with a positive voltage remaining on CA 34. If CA 34 is smaller than CB, the end result will be a voltage less than Vref(1) 30 on CB 38, with CA 34 holding a negative voltage.

In the working example, after accounting for parasitics, CA 34 is larger than CB 38 by a ratio of 8:6, and Vref is 850 mV. After charge redistribution, CA 34 keeps a voltage of about 100 mV, and CB is at a voltage of about 950 mV. In the illustrative working example, the smallest capacitor, CB 38, is the capacitor that is zeroed out at each cycle (see FIG. 3A) and then charged in each cycle (as in FIG. 3B). By only zeroing the one, relatively smaller capacitor, current consumption can be reduced.

Upon completion of charge redistribution, the method goes to FIG. 3C.

In FIG. 3C, the effective capacitance formed by the parallel capacitors CA and CB 34, 38 is now placed in series with capacitor CC 36. The output is coupled to the reference smoothing capacitor 40 to provide the reference Vref(2) 32. A resistor 44 is provided to smooth the overall reference output.

In the working example, Ceff 34, 38 initially holds a value of 950 mV. From the charging in FIG. 3A, capacitor CC 36 holds 850 mV. This gives a total of 1.8 volts of output, the desired reference voltage for Vref(2) 32. (All quantities for the working example are approximate). The capacitor 40 will maintain the reference voltage for a period of time. Typically a refresh rate is used to keep the Vref(2) 32 in a predefined range/ripple. By increasing the refresh rate, a more precise Vref(2) 32 is provided, and decreasing the refresh rate saves power.

In one example, an active implantable medical device includes a circuit as illustrated by FIGS. 2 and 3A-3C. The device may be, for example, an implantable pacemaker, defibrillator, drug pump, neurostimulator, monitor or other implantable device having electronic circuits. Such devices typically include multiple field modes for operation including a "Shelf Mode" that is intended to be a lower power operational mode for use when the device is not yet implanted. In this example, a first refresh rate is used when the device is in Shelf Mode, and a second refresh rate is used when the device is taken out of Shelf Mode and put into an Implant Mode, where the first refresh rate is lower than the second refresh rate. For example, the first refresh rate is 64 Hertz, allowing wider ripple on Vref(2) 32 during Shelf Mode, and the second refresh rate is approximately 1 kHz, narrowing the ripple on Vref(2) 32 greatly.

In another example, an implantable device may have multiple operations running off of a single secondary power supply that uses a reference voltage for level definition. In this example, if a first operation is tolerant of wider ripple and is constantly on, while a second operation is not tolerant of wide ripple but is only on periodically or occasionally, for example, then the refresh rate may be increased only when the second operation is needed. Thus, if a Memory circuit requires minimum 1.2 Volt power supply, a 1.35 Volt reference may be used to maintain the power supply with relatively wide ripple. The same reference may be used in a radio telemetry circuit as well, with 1.35 Volt reference requiring much more precision. For a power supply provided as shown in FIGS. 3A-3C, when telemetry is active, a high refresh rate would be used, and when telemetry is inactive, a low refresh rate would be used, as the increased refresh rate would avoid ripple primarily driven to leakage current.

In an alternative to the illustration in FIGS. 3A-3C, a lesser voltage output can be achieved using the following sequence (switch SW1 is omitted):

TABLE 2

| Step | Closed | Open | Purpose |
| --- | --- | --- | --- |
| A | 2, 3, 5, 6 | 4, 7 | Charge CA 34, CC 36 to Vref(1) 30; Zero CB 38; Isolate Cap 40 and Vref(2) 32 |
| B | 2, 4 | 2, 3, 5, 6, 7 | Distribute charge from CA 34 to CB 38, both reference to ground; Isolate Cap 40 and Vref(2) 32 |
| C | 2, 4, 7 | 1, 2, 3, 5, 6 | After B, provide desired voltage to Cap 40 and Vref(2) 32 via 132K resistor 44 |

In the example shown in Table 2, assuming CA and CB are of equal size, the output Vref(2) would be approximately 1.5 times Vref(1), since the charge redistribution would place equal voltages of ½ Vref(1) on each of CA 34 and CB 38. If desired, the methods shown in Table 1 and Table 2 could be used to generate multiple reference voltage outputs, as highlighted in FIG. 4.

Figure 4:
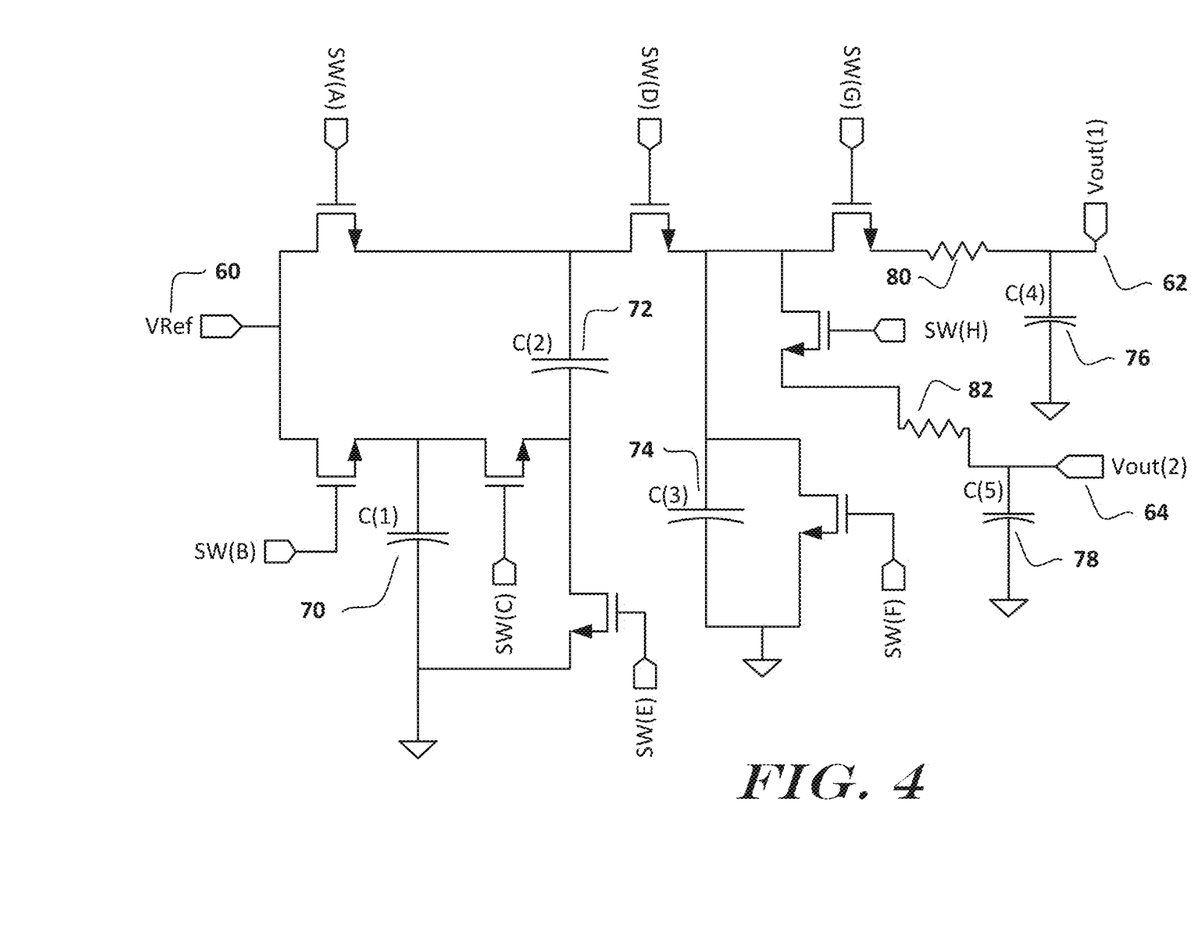
FIG. 4 shows an example providing multiple reference voltage outputs from a first reference voltage using capacitive charge redistribution.

FIG. 4 shows another illustrative example for providing multiple reference voltage outputs from a first reference voltage using capacitive charge redistribution. As shown in FIG. 4, a first Vref 60 is used to provide Vout(1) 62 and Vout(2) 64, using a network of switches SW(A), SW(B), SW(C), SW(D), SW(E) and SW(F) to manipulate Capacitors C1 70, C2 72, and C3 74, while using separate switches SW(G) and SW(H) to control which of the reference outputs are being refreshed at any given time.

Table 3 illustrates the opening and closing of switches to achieve multiple reference output:

TABLE 3

| Step | Closed | Open | Purpose |
| --- | --- | --- | --- |
| 1 | A, B, E, F | C, D, G, H | Charge C(1), C(2) to Vref, ground C(3) |
| 2 | C, D | A, B, E, F, G, H | Put C(1) and C(2) in series, distribute charge to C(3) |

TABLE 3-continued

| Step | Closed | Open | Purpose |
|------|--------|------|---------|
| 3 | C, D, G | A, B, E, F, H | Refresh C(4) to Vout(2) Nominal (higher than VRef) |
| 4 | A, E, F | B, C, E, G, H | Charge C(2), zero C(3), C(1) Floats |
| 5 | D, E | A, B, C, F, G, H | Distribute charge between C(2) and C(3) |
| 6 | D, E, H | A, B, C, F, G | Refresh C(5) to Vout(3) Nominal (lower than VRef) |
| 7 | C, D, E, F | A, B, G, H | Ground C(1), C(2) and C(3) |

Steps 1-6 allow provision of multiple power supplies of a single reference, and allow reuse of the stored energy on the capacitors, other than C(3), which is zeroed out in each half-cycle. This minimizes the current draw. Step 7 is optional and may be used periodically to fully drain and refresh of the individual capacitors throughout the circuit.

Figure 5:
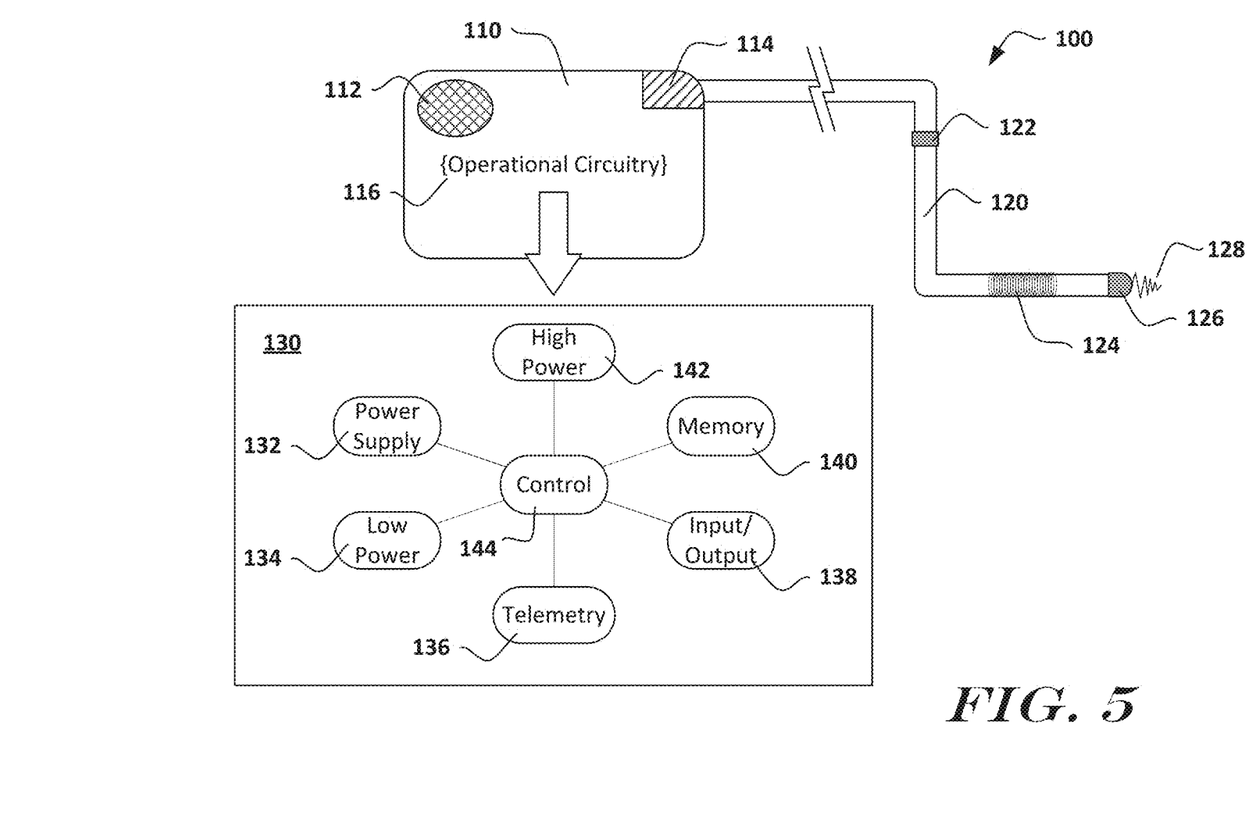
FIG. 5 depicts an illustrative implantable medical device in which the present invention may be used.

FIG. 5 depicts an illustrative implantable medical device in which the present invention may be used. The device is illustrated at 100 and includes a canister 110 and lead 120. Some illustrative features may include, for example, an electrode 112 and a header 114 for coupling removably with the lead 120. The electrode 112 may be integral with the canister 110 or it may actually be the outer shell of the canister 110. The canister 110 will typically be a hermetically sealed unit that houses operational circuitry 116 for the implantable system 100.

The operational circuitry 116 may include various elements, and some illustrations are provided at 130. Typically, there will be a power supply 132, usually having one or more batteries which may or may not be rechargeable. For example, many cardiac stimulation devices have non-rechargeable batteries, while neuromodulation devices for pain management are often rechargeable. There is usually some amount of low power circuitry 134 that can drive various functions including logic and processing, telemetry circuitry 136 with an RF radio, inductive telemetry or other technical solution (sonic, infrared) for communicating with a non-implanted external programmer, network or other device, input/output circuitry 138 for receiving, amplifying, filtering, etc. a biological signal or delivering stimulus, or operating a drug dispensing device, etc., memory 140 for storing instructions for operation as well as records of activity, observed events, treatment, status logs, etc. Systems may also include high power circuitry 142 such as the output circuitry for an implantable defibrillator. All of these elements 132-142 typically couple with one another via a control module 144 which may include a controller or processor.

There are plenty of opportunities for different reference voltages to be required by different circuits and sub-circuits. For example, an amplifier/filter circuit for conditioning a biological signal may require a low voltage reference in the range of a few hundred millivolts (850 mV, for example), while a mid-power-range telemetry circuit 136 may require a voltage reference in the range of a few volts (2.2 Volts, for example), and memory 140 may use yet another reference voltage (1.35 volts for example) for additional functions. In such a device, the biological signal circuit may be deemed most critical, so the "best" reference voltage (where the most power will be consumed) may be selected to precisely match the need of the biological signal conditioning circuit, and other, secondary references may be derived from that one reference by using circuits as shown in FIGS. 2-4, above.

The provision of each of a canister 110, with electrode 112 and header 114, and lead 120 with electrodes 122, 124, 126 and a distal attachment feature 128, as shown in FIG. 5 is merely illustrative. Other designs can also be used; for example, some implantable cardiac monitoring devices and/or so-called "seed" pacemakers have only a canister 110 and omit a lead 120. Some proposed systems include an elongated flexible housing (i.e. U.S. Pat. No. 6,647,292 (unitary subcutaneous defibrillator) or U.S. Pat. No. 7,734,343 (intravascular active medical implant) for example).

The various elements shown at 130 are not all required in any one system. For example, a device may use conducted emissions, provided through the input/output circuitry 138 and omit the telemetry circuit 136 entirely. A neuromodulation device may omit the high power circuit 142 but may include an inductive circuit for recharging its battery transcutaneously. Output circuits and high power circuitry 142 may be left out of an implantable loop recorder. The low power circuit 134 and control circuitry 144 may be combined. The indication that elements couple via control circuitry 144 is merely illustrated; in some instances the outer elements 132-142 may be directly connected together with control circuitry 144 simply controlling operation, rather than routing connections.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
   first and second operating circuits each requiring different reference voltages;
   first reference voltage circuit for producing a first reference voltage;
   a capacitive circuit comprising a plurality of capacitors and a plurality of switches arranged such that:
      in a first switch configuration, one or more of the plurality of switches is closed to couple the first reference voltage circuit to at least a first capacitor of the capacitive circuit, allowing the first capacitor to be charged from the first reference voltage circuit, and a second capacitor is discharged to ground;
      in a second switch configuration, the first capacitor is coupled to the second capacitor to allow charge distribution therebetween; and
      in a third switch configuration, a second reference voltage having a different voltage from the first reference voltage is generated by the capacitive circuit for use in the second operating circuit; and
   control circuitry configured to generate a second reference voltage different from the first reference voltage by:
   during a first time period, placing the capacitive circuit in the first switch configuration to cause the first capacitor to be charged to the first reference voltage and the second capacitor to be discharged;
   during a second time period following the first time period, placing the capacitive circuit in the second switch configuration to cause charge redistribution between the first and second capacitors; and
   during a third time period, placing the capacitive circuit in the third switch configuration to generate the second reference voltage for use by the second operating circuit;
   wherein the operational circuitry is configured to control the capacitive circuit to provide the second reference voltage as an output having a predefined ripple relative to a nominal voltage by selecting the first, second and third time periods to manipulate the ripple using the following criteria:
   while the device is in a first state, relatively low power state, allowing a first amount of ripple; and
   while the device is in a second, relatively higher power state, allowing less ripple than in the first state.

2. The implantable medical device of claim 1 wherein: the capacitive circuit includes first and third capacitors coupled with the plurality of switches such that, in the first switch configuration, the first and third capacitors are coupled in parallel to one another, and in the second switch configuration, the first and third capacitors are coupled in series with one another.

3. The implantable medical device of claim 1 wherein the capacitive circuit is configured to provide each of the second reference voltage, by use of the first, second and third switch configurations, and a third reference voltage different from the second reference voltage, using at least a fourth switch configuration.

4. The implantable medical device of claim 3 wherein the second reference voltage is larger than the first reference voltage, and the third reference voltage is smaller than the first reference voltage, and the capacitive circuit is used in alternating fashion to cyclically generate the second and third reference voltages.

5. The implantable medical device of claim 4 wherein the first operational circuit uses the third reference voltage.

6. The implantable medical device of claim 1 wherein the first operational circuit uses the first reference voltage.

7. The implantable medical device of claim 1 wherein the second operational circuit is a telemetry circuit comprising an RF generator.

8. The implantable medical device of claim 1 wherein the second operational circuit is a biological signal processing circuit comprising an amplifier.

9. The implantable medical device of claim 1 wherein the second operational circuit is a memory circuit.

10. A method of operation in implantable medical device comprising first and second operating circuits each requiring different reference voltages, a first reference voltage circuit for producing a first reference voltage, and a capacitive circuit comprising a plurality of capacitors and a plurality of switches arranged such that:
   in a first switch configuration, one or more of the plurality of switches is closed to couple the first reference voltage circuit to at least a first capacitor of the capacitive circuit, allowing the first capacitor to be charged from the first reference voltage circuit, while a second capacitor is discharged to ground;
   in a second switch configuration, the first capacitor is coupled to the second capacitor to allow charge distribution therebetween; and
   in a third switch configuration, a second reference voltage having a different voltage from the first reference voltage is generated by the capacitive circuit using the second capacitor for use in the second operating circuit;
the method comprising:
   during a first time period, placing the capacitive circuit in the first switch configuration to cause the first capacitor to be charged to the first reference voltage and the second capacitor to be discharged;
   during a second time period following the first time period, placing the capacitive circuit in the second switch configuration to cause charge redistribution between the first and second capacitors; and
   during a third time period, placing the capacitive circuit in the third switch configuration to generate the second reference voltage for use by the second operating circuit;
   wherein the capacitive circuit provides the second reference voltage as an output having a predefined ripple relative to a nominal voltage, wherein the first, second and third time periods are selected to manipulate the ripple using the following criteria:
   while the device is in a first state, relatively low power state, allowing a first amount of ripple; and while the device is in a second, relatively higher power state, allowing less ripple than in the first state.

11. The method of claim 10 wherein the capacitive circuit includes first and third capacitors coupled with the plurality of switches such that, in the first switch configuration, the first and third capacitors are coupled in parallel to one another, and in the second switch configuration, the first and third capacitors are coupled in series with one another, such that the method comprises placing the first and third capacitors in parallel with each other during the first time period, and placing the first and third capacitors in series with one another during the second time period.

12. The method of claim 10 wherein the capacitive circuit is configured to provide each of the second reference voltage, by use of the first, second and third switch configurations, and a third reference voltage different from the second reference voltage, using at least a fourth switch configuration, and the method further comprises, during a fourth time period, placing the capacitive circuit in the fourth configuration to generate the third reference voltage.

13. The method of claim 10 wherein the second reference voltage is larger than the first reference voltage, and the third reference voltage is smaller than the first reference voltage, and the capacitive circuit is used in alternating fashion to cyclically generate the second and third reference voltages.

14. The method of claim 13 wherein the first operational circuit uses the third reference voltage.

15. The method of claim 10 wherein the first operational circuit uses the first reference voltage.

16. The method of claim 10 wherein the second operational circuit is a telemetry circuit comprising an RF generator.

17. The method of claim 10 wherein the second operational circuit is a biological signal processing circuit comprising an amplifier.

18. The method of claim 10 wherein the second operational circuit is a memory circuit.

* * * * *